US009913694B2

(12) United States Patent
Brisson

(10) Patent No.: US 9,913,694 B2
(45) Date of Patent: *Mar. 13, 2018

(54) GRIP FORCE CONTROL IN A ROBOTIC SURGICAL INSTRUMENT

(75) Inventor: Gabriel F. Brisson, Albany, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 502 days.

This patent is subject to a terminal disclaimer.

(21) Appl. No.: 13/484,154

(22) Filed: May 30, 2012

(65) Prior Publication Data

US 2012/0310256 A1 Dec. 6, 2012

Related U.S. Application Data

(60) Provisional application No. 61/491,804, filed on May 31, 2011.

(51) Int. Cl.
*A61B 34/00* (2016.01)
*A61B 34/30* (2016.01)
(Continued)

(52) U.S. Cl.
CPC .............. *A61B 34/30* (2016.02); *A61B 34/37* (2016.02); *A61B 34/77* (2016.02); *A61B 2017/00477* (2013.01); *A61B 2090/064* (2016.02)

(58) Field of Classification Search
CPC ................ A61B 19/2203; A61B 17/29; A61B 2019/2249; A61B 34/30; A61B 34/77;
(Continued)

(56) References Cited

U.S. PATENT DOCUMENTS 6,424,885 B1 7/2002 Niemeyer et al.
2007/0156122 A1 7/2007 Cooper
(Continued)

FOREIGN PATENT DOCUMENTS

CN         101820824 A     9/2010
EP           1962711 A1     9/2008
WO   WO 2011108142 A1 * 9/2011

OTHER PUBLICATIONS

International Search Report and Written Opinion for Application No. PCT/US2012/040015, dated Oct. 5, 2012, 10 pages.
(Continued)

*Primary Examiner* — Katherine M Shi
*Assistant Examiner* — Michael Mendoza

(57) ABSTRACT

Surgical assemblies, instruments, and related methods are disclosed that control tissue gripping force. A surgical assembly includes an end effector including a jaw operable to grip a patient tissue and a spring assembly. The spring assembly includes an output link drivingly coupled with the jaw, an input link drivingly coupled to an articulation source, and a spring coupled with the input and output links to transfer an articulation force from the input link to the output link. The spring is preloaded to inhibit relative movement between the input link and the output link while the transferred articulation force is below a predetermined level and so as to allow relative movement between the input link and the output link when the transferred articulation force is above the predetermined level.

12 Claims, 11 Drawing Sheets

(51) Int. Cl.
    *A61B 34/37*     (2016.01)
    *A61B 17/00*     (2006.01)
    *A61B 90/00*     (2016.01)

(58) Field of Classification Search
    CPC .............. A61B 34/37; A61B 2090/064; A61B 2017/00477
    See application file for complete search history.

(56) References Cited

U.S. PATENT DOCUMENTS

| | | |
|---|---|---|
| 2008/0046122 A1 | 2/2008 | Manzo et al. |
| 2008/0306339 A1* | 12/2008 | Hashimoto .......... A61B 1/0052 600/114 |
| 2009/0088897 A1 | 4/2009 | Zhao et al. |
| 2009/0090763 A1* | 4/2009 | Zemlok ............ A61B 17/07207 227/175.2 |
| 2009/0112229 A1 | 4/2009 | Omori et al. |
| 2012/0022509 A1* | 1/2012 | Naito ................................ 606/1 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

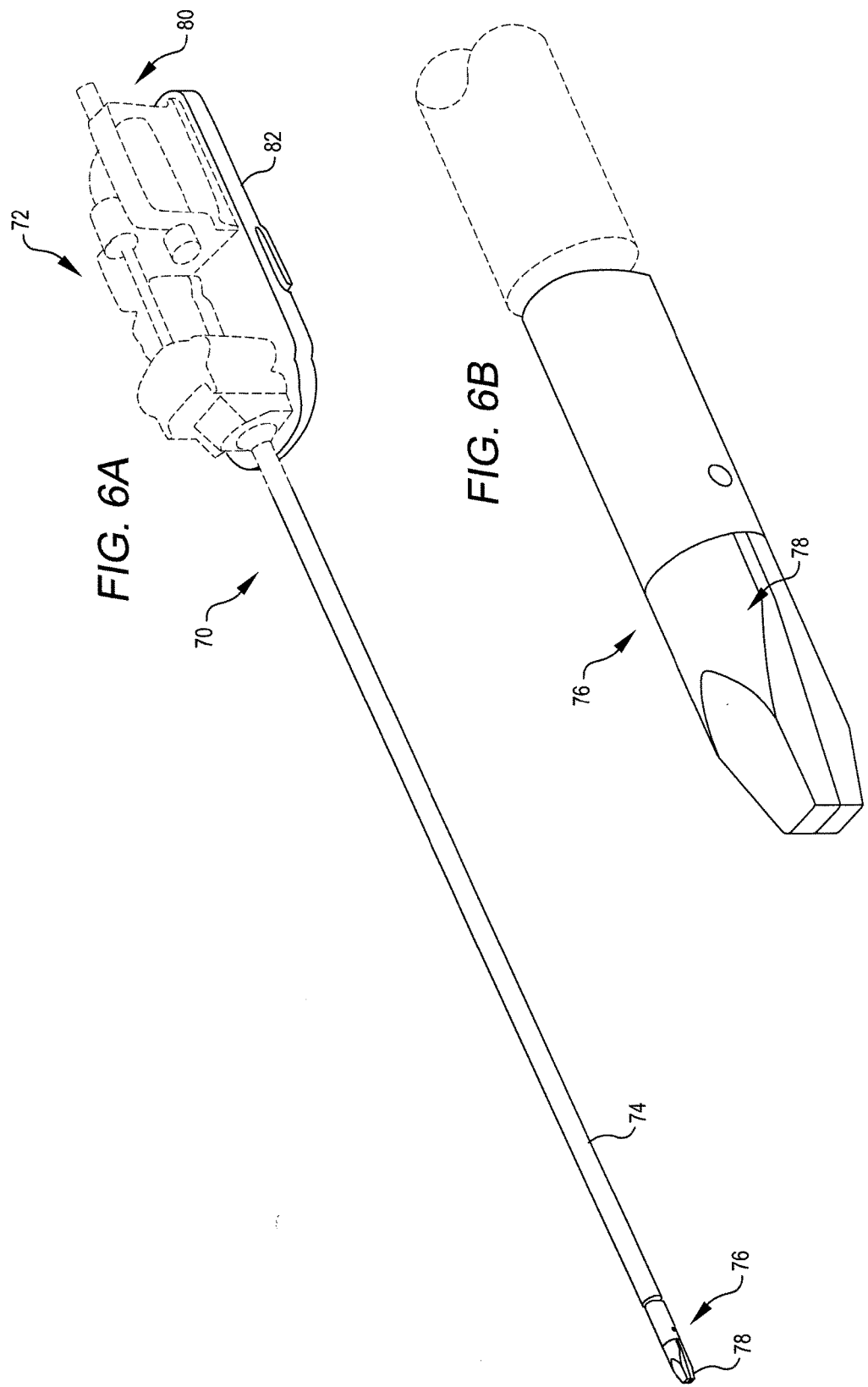

GRIP FORCE CONTROL IN A ROBOTIC SURGICAL INSTRUMENT

CROSS-REFERENCES TO RELATED APPLICATIONS

This application claims the benefit of U.S. Provisional Application No. 61/491,804, entitled "GRIP FORCE CONTROL IN A ROBOTIC SURGICAL INSTRUMENT", filed May 31, 2011, the entire disclosure of which is hereby incorporated herein by reference.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Non-robotic linear clamping, cutting and stapling devices have been employed in many different surgical procedures. For example, such a device can be used to resect a cancerous or anomalous tissue from a gastro-intestinal tract. Many known surgical devices, including known linear clamping, cutting and stapling devices, often have opposing jaws that are used to manipulate patient tissue.

For known devices having opposing jaws, a significant amount of mechanical power must be delivered to the end effector to effectively, for example, clamp tissue, staple tissue, cut tissue, etc. The delivery of the necessary amount of mechanical power can involve mechanisms having a high mechanical advantage to convert a high motion low force actuation input into a high clamping force. Such mechanisms are typically relatively stiff and capable of generating excessive amounts of clamping force. Accordingly, the use of such a high mechanical advantage mechanism may in some circumstances result in the application of an excessive clamping force that damages the tissue being clamped.

Thus, there is believed to be a need for a surgical assembly that is operable to generate clamping forces in a controlled manner.

BRIEF SUMMARY

Surgical assemblies, instruments, and related methods are disclosed that control tissue gripping force. The disclosed assemblies, instrument, and related methods employ a mechanism having a preloaded spring that biases components of the mechanism together when a force/torque transmitted to a clamping mechanism is below a predetermined level and allows separation between the components when the force/torque transmitted is above the predetermined level. The disclosed assemblies, instruments, and methods can be employed in any suitable application. For example, the surgical assemblies, instruments, and/or methods disclosed herein can be employed in other surgical instruments, manual or powered, hand-held or robotic, directly controlled or teleoperated, for open or minimally invasive (single or multi-port) procedures. The disclosed assemblies, instruments, and methods can be particularly advantageous when employed in minimally invasive robotic surgical assemblies, instruments, and procedures.

Thus, in a first aspect, a minimally invasive robotic surgical assembly is provided. The surgical assembly includes an end effector including a jaw operable to grip a patient tissue and a spring assembly. The spring assembly includes an output link drivingly coupled with the jaw, an input link drivingly coupled to an articulation source, and a spring coupled with the input and output links to transfer an articulation force from the input link to the output link. The spring is preloaded to inhibit relative movement between the input link and the output link while the transferred articulation force is below a predetermined level and so as to allow relative movement between the input link and the output link when the transferred articulation force is above the predetermined level.

In many embodiments of the surgical assembly, the transferred articulation force induces a grip force of the jaw. A movement of the input link to further close the jaw when the transferred articulation force is at or above the predetermined level induces deformation of the spring associated with the relative movement between the input link and the output link so as to control an increase in transferred articulation force while the deformed spring transfers the articulation force from the input link to the output link.

The spring of the spring assembly can be an extension spring. And linear motion of the output link relative to the end effector can be used to induce articulation of the jaw.

In many embodiments of the surgical assembly, the spring of the spring assembly includes a torsion spring. And rotational motion of the output link relative to the end effector can be used to induce articulation of the jaw. The input and output links can be rotationally mounted to a base to rotate about a common axis of rotation. For example, the output link can be fixedly attached to a central shaft and the input link rotationally mounted to the central shaft. Alternatively, the input link can be fixedly attached to a central shaft and the output link rotationally mounted to the central shaft. When the spring comprises a torsion spring, the torsion spring can be accommodated and constrained by at least one of an external surface of the input link or an external surface of the output link.

In many embodiments of the surgical assembly, the spring assembly further includes one or more interface elements rotationally mounted to the base to rotate about the common axis of rotation. The combination of the one or more interface elements and the spring inhibits relative movement between the input link and the output link while the transferred articulation force is below the predetermined level and allows relative movement between the input link and the output link when the transferred articulation force is above the predetermined level. At least one of the one or more interface elements can have a protrusion that is shaped to interface with a complementary shaped protrusion of at least one of the input link or the output link while the transferred articulation force is below the predetermined level.

In another aspect, a method for controlling grip force in a robotic surgical instrument is provided. The method includes actuating an input link of a spring assembly, transferring an actuation force from the input link to an output link of the spring assembly, inhibiting relative movement between the input link and the output link when the transferred actuation force is below a predetermined level with a preloaded spring of the spring assembly, moving the input link relative to the output link by deforming the preloaded spring of the spring assembly when the transferred actuation force increases above the predetermined level, and actuating a grip mechanism via the output link so as to grip a patient tissue.

The acts of the method can be accomplished in various suitable ways. For example, the actuation of the input link can include translating the input link relative to the grip mechanism. The actuation of the input link can include rotating the input link relative to the grip mechanism. The transfer of the actuation force can include transferring a force between the input link and the output link through a preloaded spring. The inhibition of relative movement between the input link and the output link can include constraining the input and output links relative to each other with the preloaded spring. And the inhibition of relative movement between the input link and the output link can include interfacing the input link with an interface link and interfacing the interface link with the output link, the input and output links being held in contact with the interface link by the preloaded spring. The input link, the output link, and the interface link can be constrained to rotate about a common axis of rotation. And the preloaded spring can include a torsion spring coupled between the input link and the output link.

In another aspect, a surgical instrument is provided for use with a robotic manipulator of a minimally invasive surgical system, the robotic manipulator having a holding fixture. The surgical instrument includes an instrument shaft extending between a distal end and a proximal end, an end effector supported by the distal end and including a jaw operable to grip a patient tissue, a drive element drivingly coupled with the jaw, and a chassis disposed at the proximal end. The chassis includes a frame supporting the instrument shaft, a spring assembly, and an input coupler. The spring assembly includes an output link drivingly coupled with the drive element, an input link, and a spring coupled with the input and output links to transfer an articulation force from the input link to the output link. The spring is preloaded so as to inhibit relative movement between the input link and the output link while the transferred articulation force is below a predetermined level and so as to allow relative movement between the input link and the output link when the transferred articulation force is above the predetermined level. The input coupler is drivingly coupled with the input link and configured to drivingly interface with a corresponding output coupler of the robotic manipulator.

In many embodiments of the surgical instrument, the transferred articulation force induces a grip force of the jaw. And a movement of the input link to further close the jaw when the transferred articulation force is at or above the predetermined level induces deformation of the spring associated with the relative movement between the input link and the output link so as to control an increase in transferred articulation force while the deformed spring transfers the articulation force from the input link to the output link.

In many embodiments of the surgical instrument, the drive element includes a drive shaft rotationally coupled with the grip mechanism. The input link and the output link can be rotationally mounted to the frame to rotate about a common axis of rotation. And the preloaded spring can include a torsion spring.

In many embodiments of the surgical instrument, the spring assembly further includes one or more interface elements rotationally mounted to the base to rotate about the common axis of rotation. The combination of the one or more interface elements and the spring inhibits relative movement between the input link and the output link while the transferred articulation force is below the predetermined level and allows relative movement between the input link and the output link when the transferred articulation force is above the predetermined level. At least one of the one or more interface elements can have a protrusion that is shaped to interface with a complementary shaped protrusion of at least one of the input link or the output link while the transferred articulation force is below the predetermined level.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 6A is a perspective view of a robotic surgery tool that includes an end effector having opposing clamping jaws, in accordance with many embodiments.

FIG. 6B is a close-up perspective view of the end effector of FIG. 6A.

DETAILED DESCRIPTION

In the following description, various embodiments of the present invention will be described. For purposes of expla- nation, specific configurations and details are set forth in order to provide a thorough understanding of the embodi- ments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
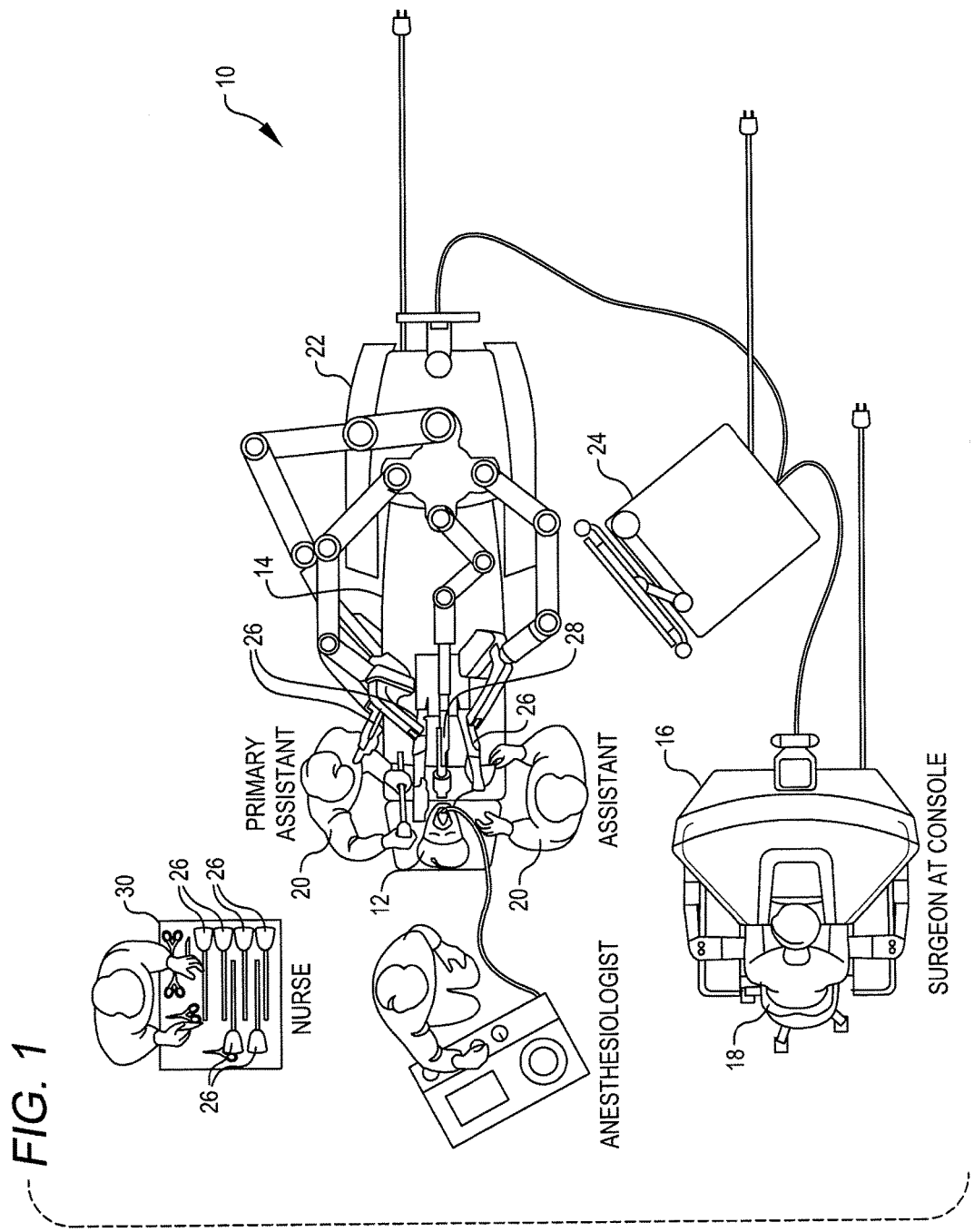
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Oper- ating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endo- scope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
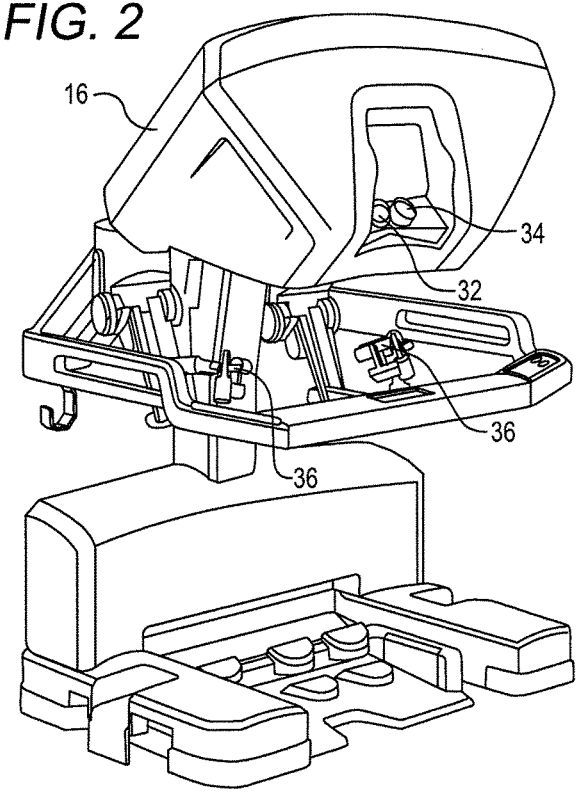
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
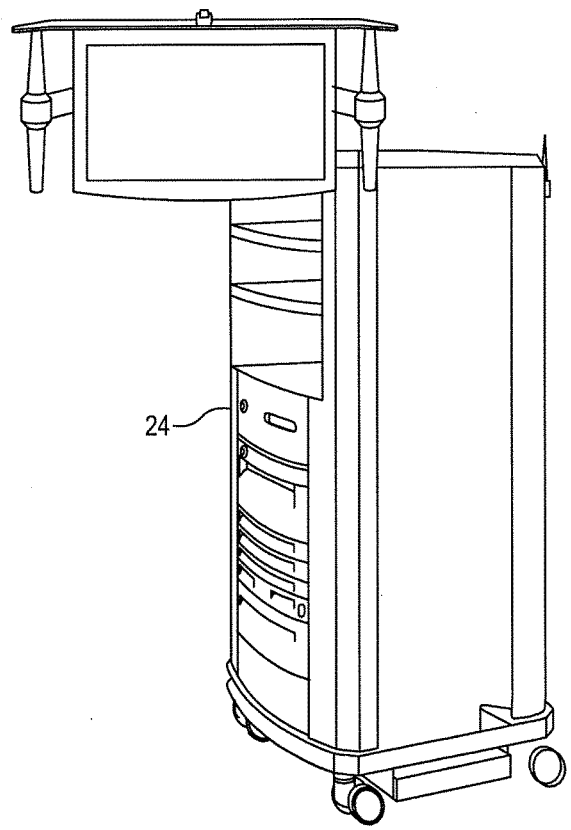
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Sur- geon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
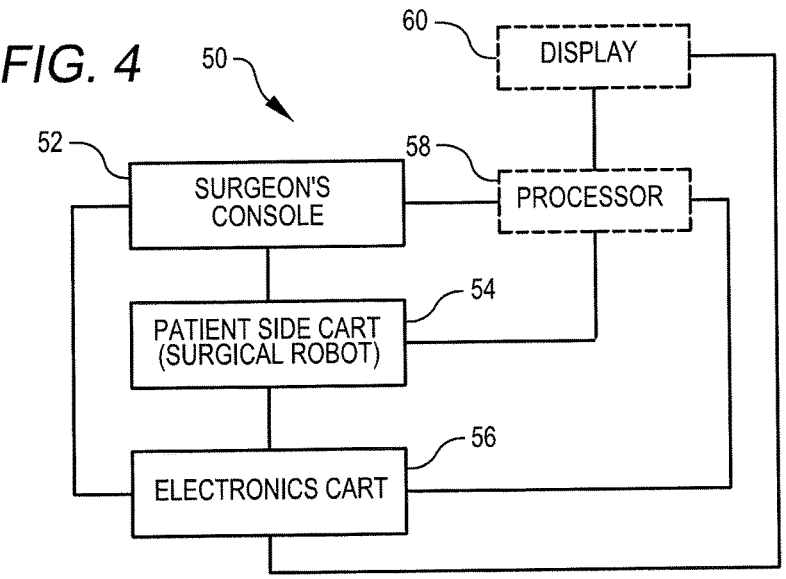
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
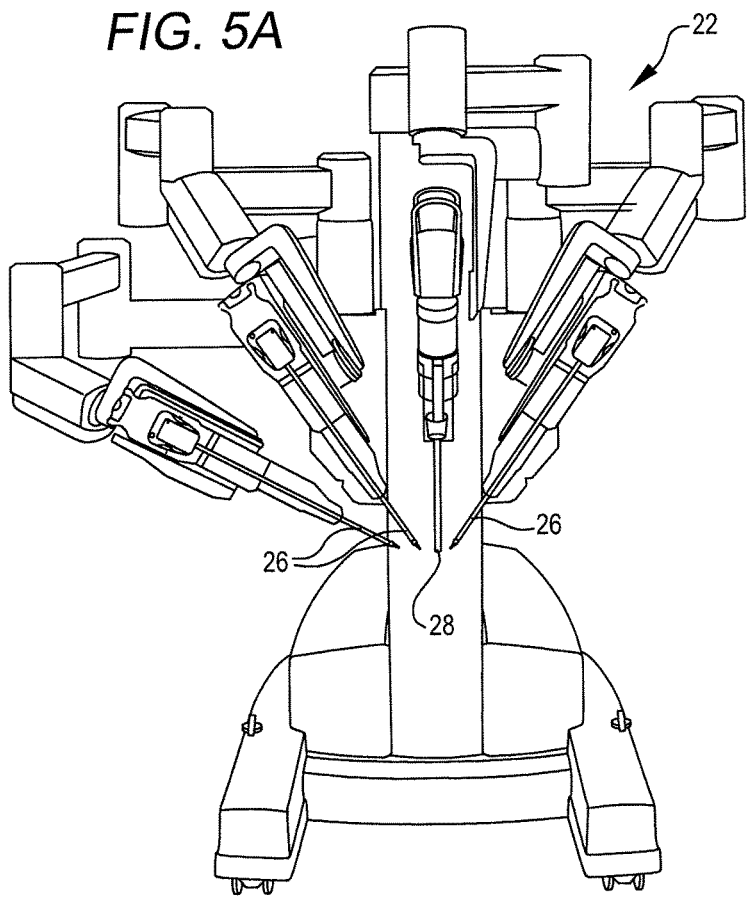
FIG. 5A is a front view of a patient side cart (surgical robot) of a robotic surgery system, in accordance with many embodiments.
Figure 5B:
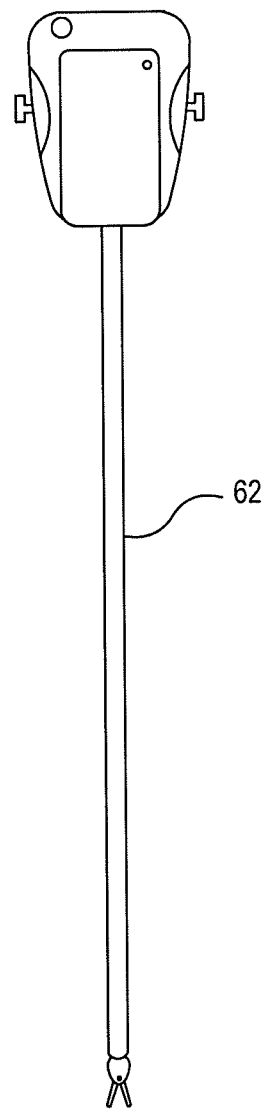
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Tissue Gripping End Effectors

FIG. 6A shows a surgical tool 70 that includes a proximal chassis 72, an instrument shaft 74, and a distal end effector 76 having a jaw 78 that can be articulated to grip a patient tissue. The proximal chassis includes an input coupler that is configured to interface with and be driven by an output coupler of the Patient Side Cart 22. The input coupler is drivingly coupled with an input link of a spring assembly 80. The spring assembly 80 is mounted to a frame 82 of the proximal chassis 72 and includes an output link that is drivingly coupled with a drive shaft that is disposed within the instrument shaft 74. The drive shaft is drivingly coupled with the jaw 78. FIG. 6B provides a close-up view of the jaw 78 of the end effector 76.

Figure 7:
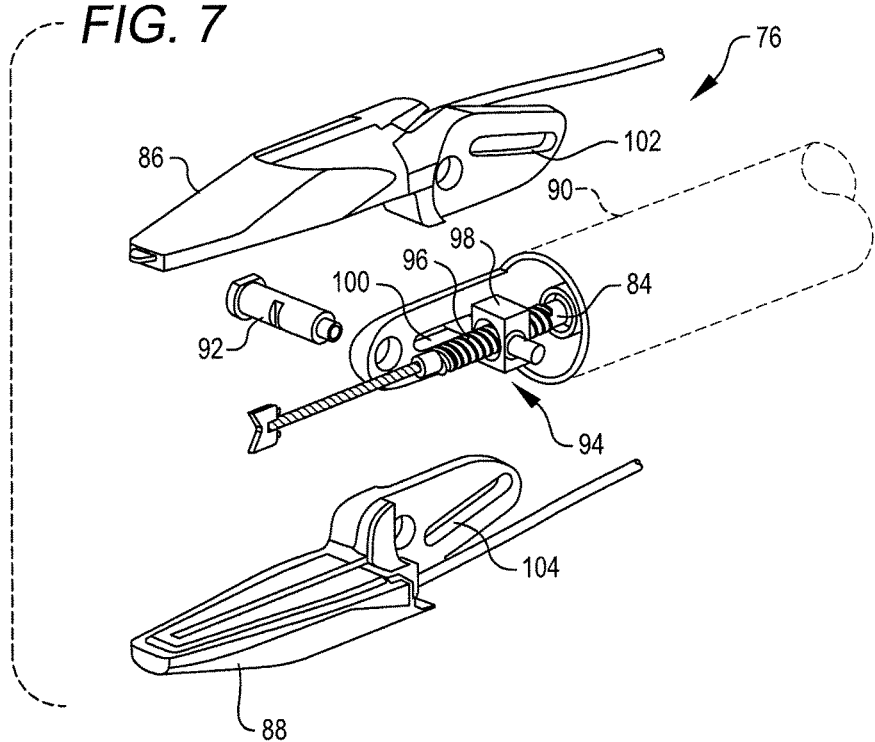
FIG. 7 is an exploded perspective view of the end effector of FIG. 6A, illustrating a mechanism used to convert rotary motion of a drive shaft into articulation of the opposing clamping jaws.

FIG. 7 is an exploded perspective view of the end effector 76 of FIG. 6A, illustrating a clamping mechanism used to convert rotary motion of a drive shaft 84 into articulation of opposing clamping jaws of the end effector 76. The end effector includes an upper jaw 86, a lower jaw 88, a frame 90, a pin 92 for pivotally mounting the upper jaw 86 and the lower jaw 88 to the frame 90, and a lead screw mechanism 94 that is drivingly coupled with the drive shaft 84. The lead screw mechanism 94 includes a lead screw 96 and a mating translating nut 98 that is advanced and retracted along a slot 100 in the frame 90 via rotation of the lead screw 96. The translating nut 98 includes oppositely extending protrusions that interface with a slot 102 in the upper jaw 86 and with a slot 104 in the lower jaw 88, thereby causing articulation of the upper jaw 86 and the lower jaw 88 about the pin 92 when the translating nut 98 is advanced or retracted along the slot 100.

Figure 8A:
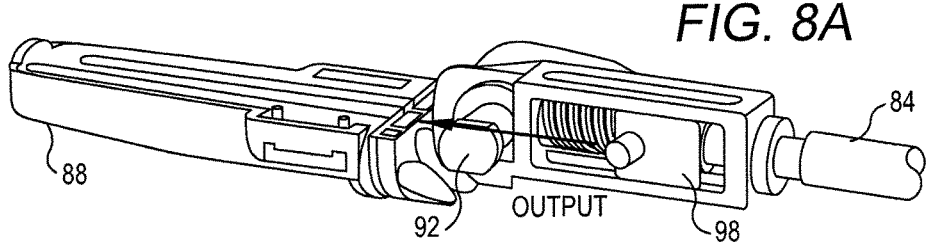
FIGS. 8A and 8B are perspective views of an end effector having opposing clamping jaws and a mechanism used to convert rotary motion of a drive shaft into articulation of the opposing clamping jaws, in accordance with many embodiments.
Figure 8B:
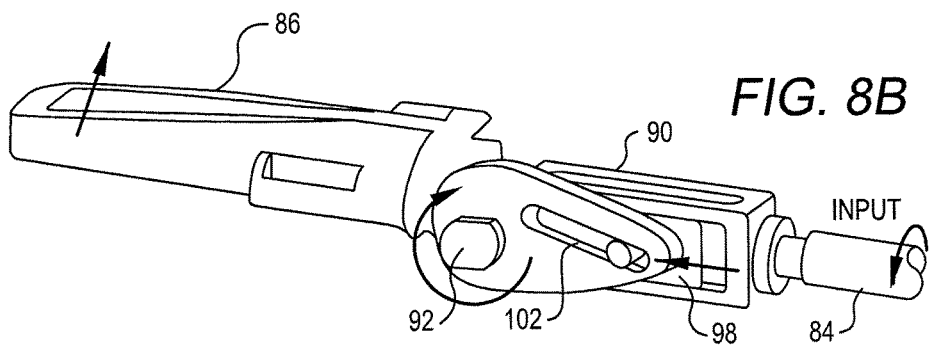

FIG. 8A and FIG. 8B illustrate the operation of a clamping mechanism similar to the clamping mechanism of FIG. 7. Rotating the drive shaft 84 in the direction shown causes a translating nut 98 to advance distally toward the pivot pin 92 by which the lower jaw 88 and the upper jaw 86 are pivotally mounted to the frame 90 of an end effector. As illustrated in FIG. 8B, a protrusion of the translating nut 98 engages the slot 102 in the upper jaw 86. Distal advancement of the translating nut 98 toward the pivot pin 92 causes the upper jaw to rotate in the direction shown, and causes the lower jaw 88 to rotate in the opposite direction, thereby opening the jaw. Similarly, proximal advancement of the translating nut 98 away from the pivot pin 92 cause the jaw to close. Accordingly, the jaw can be articulated to grip a patient tissue.

The lead screw type clamping mechanisms shown in FIG. 7, FIG. 8A, and FIG. 8B provide a substantial mechanical advantage, which converts a relatively low torque transmitted by the drive shaft into a relatively high clamping force. To avoid subjecting tissue to an excessive clamping force via a mechanism having such a substantial mechanical advantage, the torque transmitted into the clamping mechanism by the drive shaft can be controlled.

Control of Actuation Force/Torque

Figure 9:
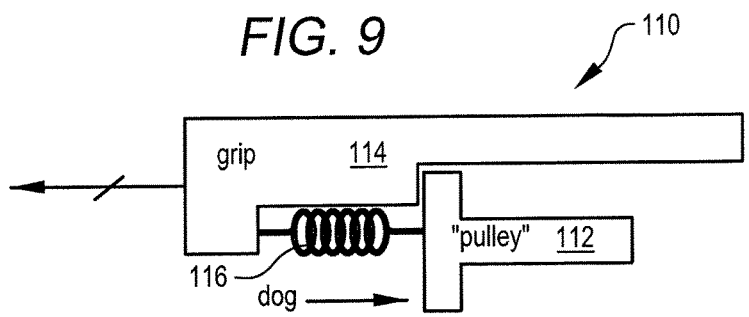
FIG. 9 is a simplified schematic illustrating an approach for controlling clamping forces in a surgical instrument, in accordance with many embodiments.

FIG. 9 schematically illustrates a spring assembly 110 for controlling the amount of clamping force that is transmitted to a jaw of an end effector. The spring assembly 110 includes an input link 112 that is driven by an input coupler (also known as "dog"), an output link 114 that is drivingly coupled with the end effector jaw, and a preloaded extension spring 116 coupled between the input link 112 and the output link 114. With reference to FIG. 9, when the input link 112 is driven to the right by the input coupler, the extension spring 116 pulls the output link 114 to the right, thereby causing the jaw of the end effector to close. As the jaw begins to grip a tissue, the force necessary to further close the jaw begins to increase. To further close the jaw, the clamping force transmitted to the jaw is increased. As the jaw continues to close, the increasing clamping force transmitted to the jaw reaches a level equal to the force in the preloaded extension spring 116. At that point, further movement of the input link 112 to the right causes the preloaded extension spring 116 to start to extend, thereby allowing the input link and the output link to begin to separate. The resulting clamping force that is transmitted to the jaw is thereafter limited by the combination of the spring rate and the total deflection of the extension spring 116.

Figure 10:
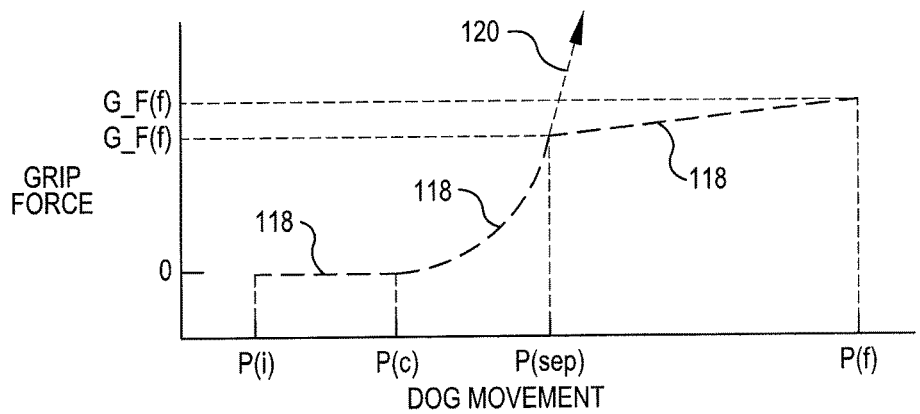
FIG. 10 graphically illustrates an approach for controlling clamping forces in a surgical instrument, in accordance with many embodiments.

FIG. 10 graphically illustrates the clamping force (also known as "grip force") transmitted through the spring assembly 110 to the end effector jaw as the input coupler moves from an initial position (P(i)) where the jaw is not gripping a tissue, to a contact position (P(c)) where the jaw begins to grip the tissue, to an intermediate position (P(sep)) where the force transmitted through the spring assembly 110 reaches the point where the preloaded extension spring 116 starts to extend, and finally to a final position (P(f)). When the input coupler is moving between the initial position (P(i)) to the contact position (P(c)), the force 118 transmitted through the spring assembly 110 remains low because the end effector jaw has not yet begun to grip the tissue. Once the end effector jaw begins to grip the tissue (when the input coupler reaches the contact position (P(c))), further movement of the input coupler to the right causes the force 118 transmitted through the spring assembly 110 to increase at a rate that depends upon the resistance offered by the tissue being gripped. When the force transmitted through the spring assembly reaches a predetermined level (G_F(i)), the preloaded extension spring 116 starts to extend, thereby controlling the amount of the force 118 that is transmitted through the spring assembly 110 as the input coupler continues to move to the right between the intermediate position (P(sep)) and the final position (P(f)). In the absence of the spring assembly 110, further movement of the input coupler between the intermediate position (P(sep)) and the final position (P(f)) would generate an uncontrolled clamping force 120, which exceeds the maximum controlled clamping force (G_F(f)) that is transferred through the spring assembly 110 when the input coupler reaches the final position (P(f)).

Figure 11:
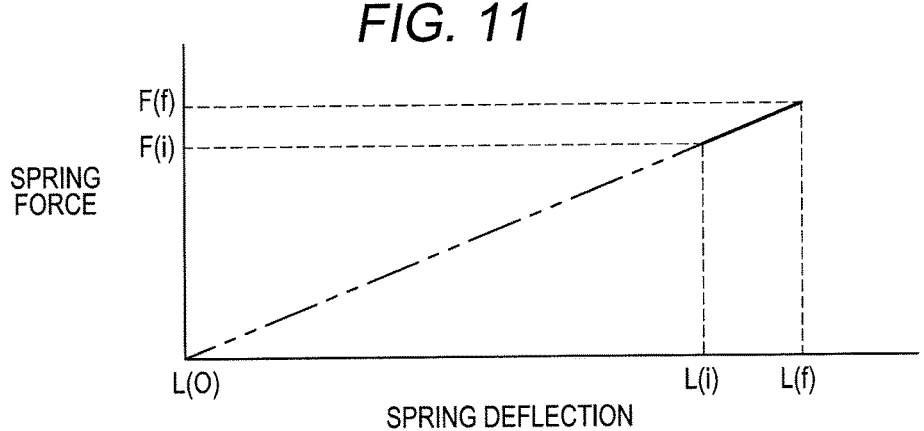
FIG. 11 graphically illustrates a working range of an extension spring used in an approach for controlling clamping forces in a surgical instrument, in accordance with many embodiments.

FIG. 11 graphically illustrates the force in the preloaded extension spring 116 during the movement of the input coupler between the initial position (P(i)) and the final position (P(f)). At zero deflection (L(0)) of the extension spring 116, the extension spring generates zero spring force. In the spring assembly 110, the extension spring 116 is in a preloaded state, thereby biasing the input link and the output link together for transmitted torques less than and equal to the predetermined level. Therefore, during the movement of the input coupler between the initial position (P(i)) and the intermediate position (P(sep)), no extension of the extension spring 116 occurs (i.e., the spring deflection remains a constant L(i)) and the generated spring force remains constant at F(i). As the input coupler moves from the intermediate position (P(sep)) to the final position (P(f)), the spring deflection of the extension spring 116 increases from L(i) to L(f), thereby increasing the spring force from F(i) to F(f). Accordingly, the force transmitted to the jaw when the input coupler moves from the intermediate position (P(sep)) to the final position (P(f)) is a function of the spring preload force (F(i)), the spring rate of the extension spring 116, and the amount of deflection of the extension spring 116 from L(i) to L(f).

Figure 12A:
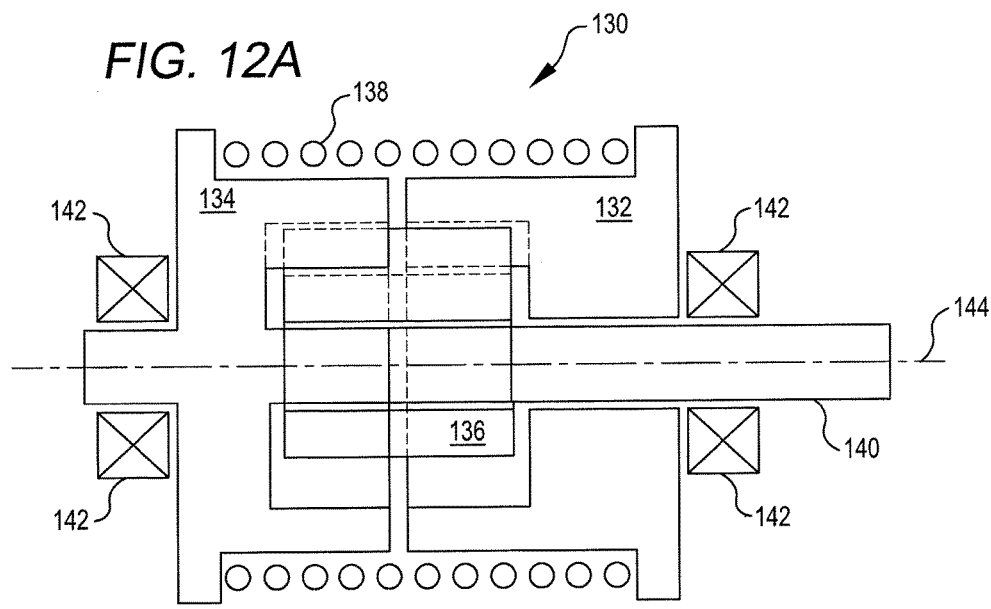
FIG. 12A is a cross-sectional view of a rotary mechanism used to control clamping forces in a surgical instrument, in accordance with many embodiments.

FIG. 12A schematically illustrates a torsion spring assembly 130 for controlling the amount of clamping force that is transmitted to a jaw of an end effector. The torsion spring assembly 130 includes an input link 132 that is rotationally coupled with an input coupler (also known as "dog"), an output link 134 that is rotationally coupled with a drive shaft that is drivingly coupled with the end effector jaw, an interface element 136, and a torsion spring 138 coupled between the input link 132 and the output link 134. The output link 134 is fixedly attached to (or integral with) a central shaft 140. The torsion spring assembly 130 is rotationally mounted to the frame 82 of the proximal chassis 72 via shaft bearings 142. The input link 132 and the interface element 136 are mounted to rotate about a central axis 144 of the central shaft 140. The torsion spring 138 coupled between the input link 132 and the output link 134 is in a preloaded state.

Figure 12B:
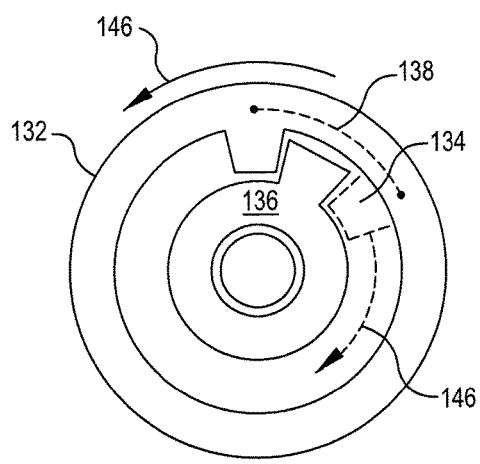
FIG. 12B is a simplified schematic illustrating a configuration of components of the rotary mechanism of FIG. 12A when the torque transmitted through the rotary mechanism is less than a predetermined level.
Figure 12C:
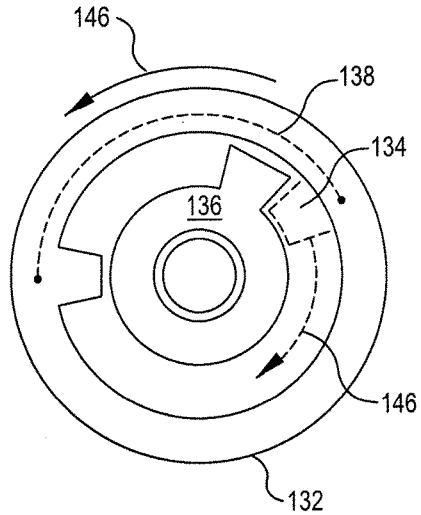
FIG. 12C is a simplified schematic illustrating a configuration of components of the rotary mechanism of FIG. 12A when the torque transmitted through the rotary mechanism is more than the predetermined level.

In operation the torsion spring assembly 130 transmits torque from the input link 132 to the output link 134. Referring to FIG. 12B, when the transmitted torque 146 is below a predetermined level (i.e., the torsion preload in the torsion spring 138), the level of preload in the torsion spring 138 is sufficient to bias the output link 134 into contact with the interface element 136, which in turn is biased into contact with the input link 132. Referring to FIG. 12C, when the transmitted torque 146 exceeds the predetermined level, the level of preload in the torsion spring 138 is insufficient to maintain the contact between the output link 134, the interface element 136, and the input link 132, and as a result additional rotational deformation of the torsion spring 138 occurs. And when the transmitted torque 146 exceeds the predetermined level, the torque transmitted through the torsion spring assembly 130 is transmitted through the torsion spring 138.

The interface element 136 serves a number of purposes. Contact between the interface element 136 and the input and output links 132, 134 maintains a relative angular orientation between the input link 132 and the output link 134 for torques transmitted through the torsion spring assembly 130 that are less than the predetermined level. The interface element 136 also serves to increase the amount of possible angular deflection that can occur between the input link 132 and the output link 134 for torques transmitted through the torsion spring assembly 130 that exceed the predetermined level. For example, the torsion spring assembly 130 can be configured without an interface element by configuring the input and output links with features that provide for direct contact between input and output links analogous to the contact provided by the interface element (e.g., the interface element 136 could be made integral to the input link 132, or the interface element 136 could be made integral to the output link 134). In such embodiments without an interface element 136, the amount of possible angular deflection that can occur between the input link 132 and the output link 134 may be limited to something slightly less than 360 degrees (e.g., approximately 345 degrees). With an interface element 136, which can rotate about the central axis 144, the amount of possible angular deflection that can occur between the input link 132 and the output link 134 may be greater (e.g., approximately 690 degrees). Any suitable number of interface elements 136 (e.g., 0, 1, 2, 3 or more, etc.) can be used appropriate for the amount of possible angular deflection desired between the input link 132 and the output link 134.

The torsion spring assembly 130, like the extension spring assembly 110, is configured to control the amount of transmitted torque/force in one direction (e.g., in the direction corresponding to closing of the end effector jaw. For torques/forces transmitted in the direction corresponding to opening of the end effector jaw, the direction of transmitted torques/forces further adds to the preloaded spring forces in preventing relative movement between the input link 132 and the output link 134. To achieve bi-directional control, an oppositely configured torsion spring assembly (i.e., one that controls torque in the direction corresponding to opening of the end effector jaw) can be added in series with the torsion spring assembly 130.

Figure 13:
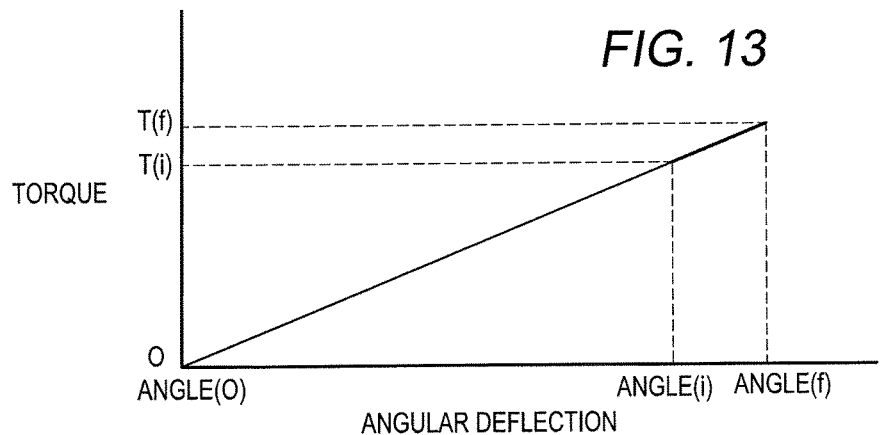
FIG. 13 graphically illustrates a working range of a torsion spring used in an approach for controlling clamping forces in a surgical instrument, in accordance with many embodiments.

Referring back to FIG. 10 and the related discussion, FIG. 13 graphically illustrates the torque in the torsion spring 138 during a rotation of the input coupler between an initial angular orientation (corresponding to P(i) in FIG. 10) and a final angular orientation (corresponding to P(f) in FIG. 10).

At zero angular deflection (ANGLE(0)) of the torsion spring 138, the torsion spring generates zero spring torque. In the torsion spring assembly 130, the torsion spring 138 is in a preloaded state, thereby biasing the input link and the output link together for transmitted torques less than and equal to the predetermined level. Therefore, during the rotation of the input coupler between the initial angular orientation and an intermediate angular orientation (corresponding to P(sep) in FIG. 10), no angular deflection of the torsion spring 138 occurs (i.e., the spring angular deflection remains a constant ANGLE(i)) and the generated spring torque remains constant at T(i). As the input coupler moves from the intermediate angular orientation to a final angular orientation (corresponding to P(f) in FIG. 10), the angular deflection of the torsion spring 138 increases from ANGLE(i) to ANGLE(f), thereby increasing the spring torque from T(i) to T(f). Accordingly, the torque transmitted to the jaw when the input coupler moves from the intermediate position to the final position is a function of the spring preload torque (T(i)), the spring rate of the torsion spring 138, and the amount of angular deflection of the torsion spring 138 from ANGLE(i) to ANGLE(f).

Figure 14:
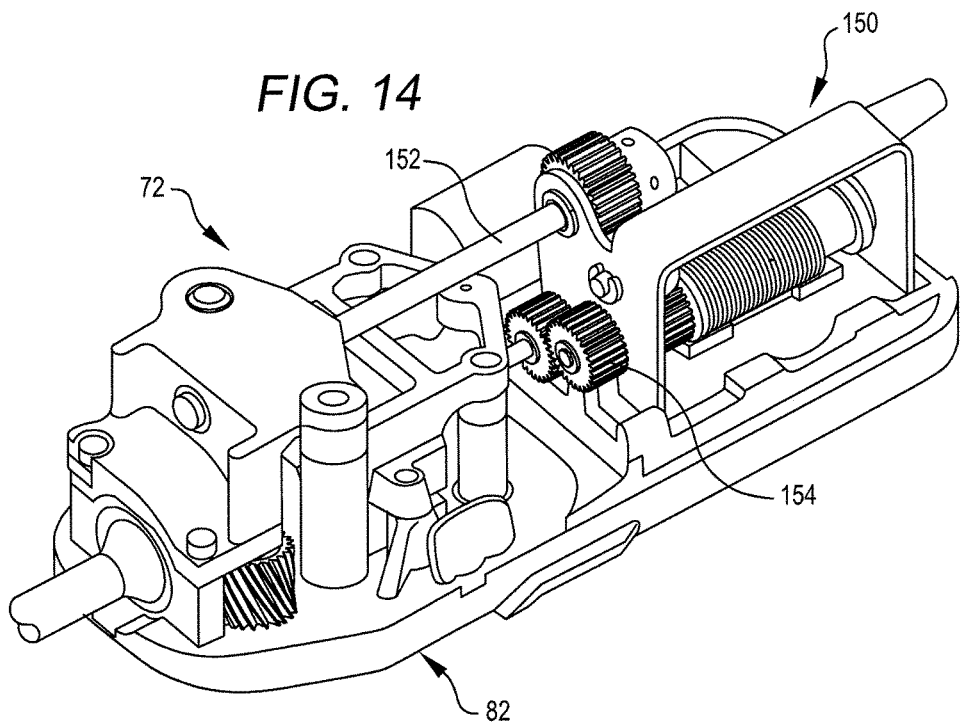
FIG. 14 is a perspective view of a proximal chassis of a robotic surgical tool, showing a rotary mechanism for controlling torque transferred to a drive shaft used to actuate clamping jaws of an end effector, in accordance with many embodiments.

FIG. 14 shows the proximal chassis 72 of the robotic surgical tool 70. The proximal chassis 72 includes the frame 82 and input couplers (not shown) that drivingly interface with corresponding output couplers of a surgical robot as illustrated in FIG. 5A. Mounted to the frame 82 is a torsion spring assembly 150 that controls the amount of torque that is transmitted to actuate the end effector jaw. The torsion spring assembly 150 receives an input torque via an input drive shaft 152 that is drivingly coupled with a corresponding one of the input couplers and delivers an output torque via an output pinion gear 154 that is drivingly coupled with the end effector jaw via an internal drive shaft that is disposed with a lumen of the instrument shaft 74 supporting the end effector 76.

Figure 15A:
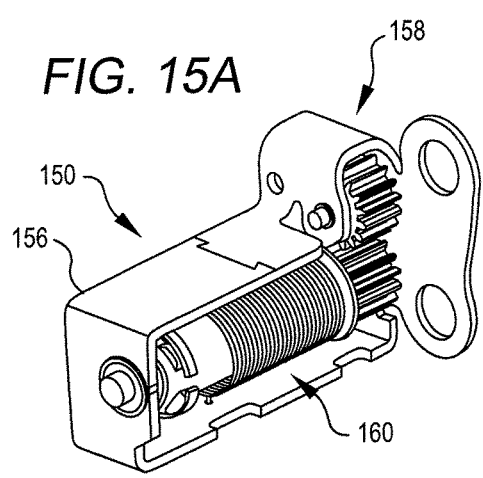
FIG. 15A is a perspective view of a rotary mechanism for controlling torque transferred to a drive shaft used to actuate clamping jaws of an end effector, in accordance with many embodiments.
Figure 15B:
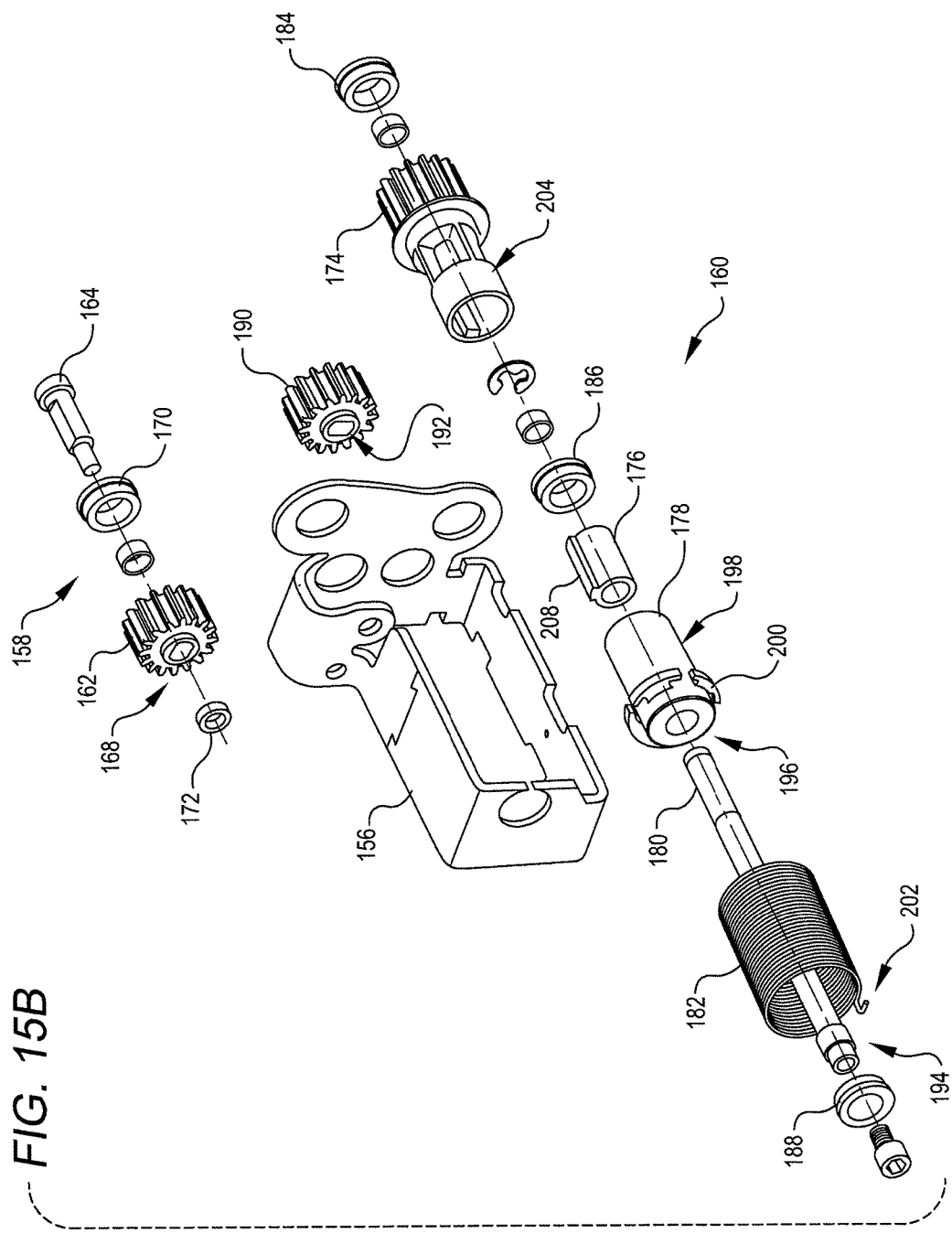
FIG. 15B is an exploded perspective view of the rotary mechanism of FIG. 15A.

FIG. 15A shows the torsion spring assembly 150 in isolation. And FIG. 15B shows an exploded view of components of the torsion spring assembly 150. The torsion spring assembly 150 includes a housing 156 that mounts to the frame 82 of the proximal chassis 72. The housing 156 supports subassemblies of the torsion spring assembly 150, including an input pinion subassembly 158 and a torque controlling subassembly 160.

The input pinion subassembly 158 includes an input pinion 162 that transfers torque received from the input drive shaft 152 to the torque controlling subassembly 160. The input pinion 162 is supported by a pin 164. The pin 164 has a flat outer portion 166 and the input pinion 162 has an aperture 168 shaped to interface with the pin 164 and the flat outer portion 166 of the pin so as to rotate with the pin 164. The pin 164 is mounted to the housing via bearings 170, 172.

The torque controlling subassembly 160 includes an input link 174, an interface element 176, an output link 178, a support shaft 180, a torsion spring 182, support bearings 184, 186, 188, and an output pinion 190. The support shaft 180 is mounted to rotate relative to the housing 156 via the bearings 184, 188. The output pinion 190 is supported by the support shaft 180 and includes an aperture 192 that is shaped to prevent rotation of the output pinion 190 relative to the support shaft 180, thereby causing the output pinion 190 to rotate with the support shaft 180. The output link 178 is supported by the support shaft 180. The support shaft 180 has a protruding shaped portion 194. The output link 178 has an aperture 196 that is shaped to interface with the support shaft 180 and its protruding shaped portion 194 so as to rotate with the support shaft 180. The output link 178 has a cylindrical outer surface 198 sized to accommodate and support the torsion spring 182. The output link 178 also has four protrusions 200 that are configured to interface with an end 202 of the torsion spring 182 to rotationally couple the torsion spring 182 and the output link 178. The input link 174 is supported by the support shaft 180 to rotate relative to the support shaft 180. The input link 174 has a cylindrical outer surface 204 sized to accommodate and support the torsion spring 182. The interface element 176 is supported by the support shaft 180 to rotate relative to the support shaft 180. The interface element 176 includes a longitudinal protrusion 208 that interfaces with internally-protruding portions of the input and output links. The torsion spring 182 is installed in a preloaded configuration, thereby rotationally biasing the input and output links into contact with the longitudinal protrusion 208 of the interface element 176 when the torque transmitted through the torque controlling subassembly 160 is less than the preload torque of the torsion spring 182.

Figure 15C:
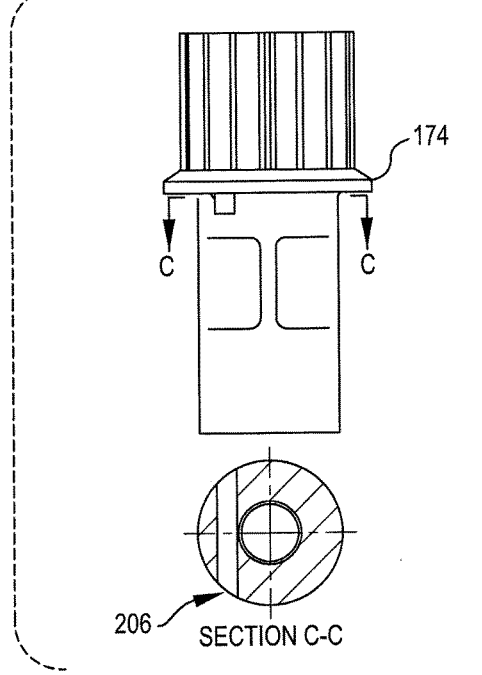
FIG. 15C illustrates details of an input link for coupling a torsion spring to the input link in the rotary mechanism of FIG. 15A.

FIG. 15C illustrates how the input link 174 is configured to couple with the torsion spring 182. As shown in section C-C, the input link 174 has a hole 206 that receives a bent end of the torsion spring 182, thereby coupling the end of the torsion spring 182 to the input link 174.

In operation, the torque controlling assembly 160 controls the level of torque that is transferred to the end effector jaw via the output pinion 190 by using the same approach used by the torsion spring assembly 130 of FIGS. 12A, 12B, and 12C. For example, for a transmitted torque that is less than the preload torque of the torsion spring 182, the output link 178 rotates at the same rate as the input link 174. When the transmitted torque exceeds the preload torque of the torsion spring 182, any additional increase in the transmitted torque results in additional angular deflection of the torsion spring 182, which allows the output link 178 to rotate at a slower rate than the input link 174, thereby controlling the amount of torque that is transmitted to the end effector jaw, which in turn controls the amount of grip force of the end effector jaw.

Applications

The surgical assemblies and instruments disclosed herein can be employed in any suitable application. For example, the surgical assemblies disclosed herein can be employed in other surgical instruments, manual or powered, hand-held or robotic, directly controlled or teleoperated, for open or minimally invasive (single or multi-port) procedures.

Methods for Controlling Grip Force in a Surgical Instrument

Figure 16:
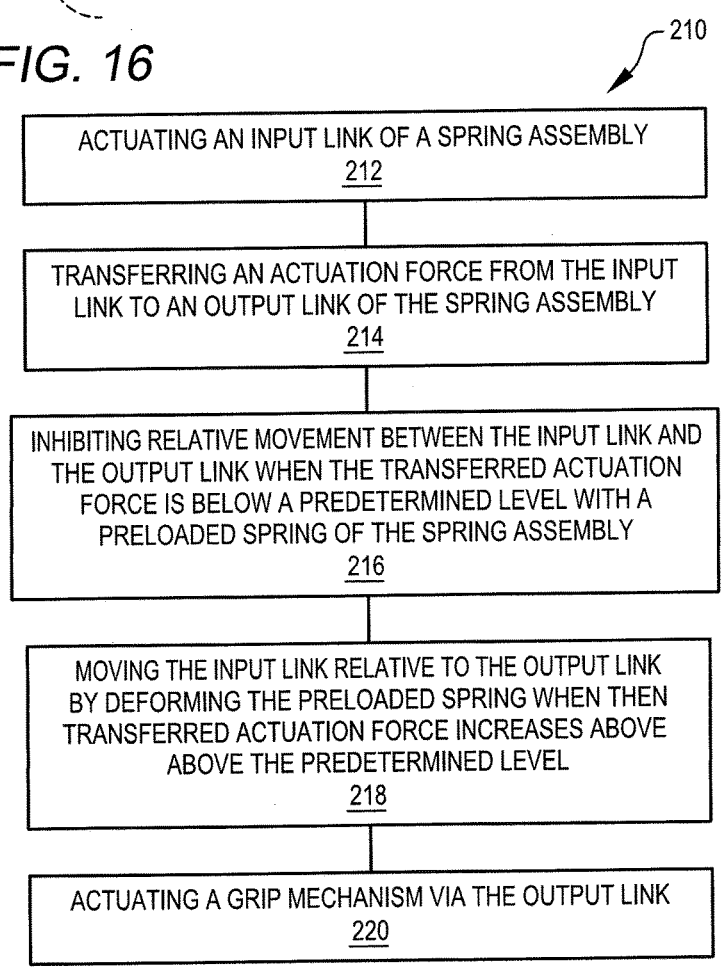
FIG. 16 illustrates acts of a method for controlling grip force in a surgical instrument, in accordance with many embodiments.

FIG. 16 illustrates acts of a method 210 for controlling grip force in a surgical instrument, in accordance with many embodiments. The method 210 can be practiced, for example, by using any of the surgical assemblies and instruments disclosed herein.

The method 210 includes actuating an input link of a spring assembly (act 212). For example, the actuation of an input link can include translating the input link relative to a grip mechanism of a surgical instrument. As another example, the actuation of an input link can include rotating the input link relative to a grip mechanism of a surgical instrument.

The method 210 further includes transferring an actuation force from the input link to an output link of the spring assembly (act 214). The transfer of the actuation force can include transferring a force between the input link and the output link through a preloaded spring of the spring assembly.

The method 210 further includes inhibiting relative movement between the input link and the output link when the transferred actuation force is below a predetermined level with the preloaded spring of the spring assembly (act 216). The inhibition of the relative movement can include constraining the input link and the output links relative to each other with the preloaded spring. And the inhibition of the relative movement can include interfacing the input link with an interface link and interfacing the interface link with the output link, the input and output links being held in contact with the interface link by the preloaded spring. In many embodiments, the input link, the output link, and the interface link are constrained to rotate about a common axis of rotation, and the preloaded spring includes a torsion spring coupled between the input link and the output link.

The method 210 further includes moving the input link relative to the output link by deforming the preloaded spring when the transferred actuation force increases above the predetermined level (act 218). And the method 210 further includes actuating a grip mechanism via the output link (act 220). In many embodiments, the grip mechanism is actuated so as to grip a patient tissue.

Method Applications

The methods disclosed herein can be employed in any suitable application. For example, the methods disclosed herein can be employed in surgical instruments, manual or powered, hand-held or robotic, directly controlled or tele-operated, for open or minimally invasive (single or multi-port) procedures. Examples of such surgical instruments include minimally invasive robotic surgical instruments such as those described herein.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A minimally invasive robotic surgical assembly comprising:
    an end effector including a jaw operable to grip a patient tissue; and
    a spring assembly including an output link drivingly coupled with the jaw to induce a grip force of the jaw, an input link drivingly coupled with an articulation source, and a spring having a first end and a second end, the first end being connected to the input link, the second end being connected to the output link, the spring assembly being configured to transfer an articulation force from the input link to the first end of the spring and transfer the articulation force from the second end of the spring to the output link, the output link being configured to transmit the articulation force to the jaw to induce the grip force of the jaw, the spring being preloaded to inhibit relative movement between the input link and the output link while the transferred articulation force is below a predetermined level and so as to allow relative movement between the input link and the output link when the transferred articulation force is above the predetermined level; and wherein rotational motion of the output link relative to the end effector induced articulation of the jaw.

2. The surgical assembly of claim 1, wherein:
    a movement of the input link to further close the jaw when the transferred articulation force is at or above the predetermined level induces deformation of the spring associated with the relative movement between the input link and the output link so as to control an increase in transferred articulation force while the deformed spring transfers the articulation force from the input link to the output link.

3. The surgical assembly of claim 1, wherein the input and output links are rotationally mounted to a base to rotate about a common axis of rotation.

4. The surgical assembly of claim 3, wherein the output link is fixedly attached to a central shaft and the input link is rotationally mounted to the central shaft.

5. The surgical assembly of claim 3, wherein the input link is fixedly attached to a central shaft and the output link is rotationally mounted to the central shaft.

6. The surgical assembly of claim 3, wherein the spring comprises a torsion spring that is accommodated and constrained by at least one of an external surface of the input link or an external surface of the output link.

7. The surgical assembly of claim 3, wherein the spring assembly further includes an interface element rotationally mounted to the base to rotate about the common axis of rotation, the combination of the interface element and the spring inhibiting relative movement between the input link and the output link while the transferred articulation force is below the predetermined level and allowing relative movement between the input link and the output link when the transferred articulation force is above the predetermined level.

8. The surgical assembly of claim 7, wherein the interface element has a protrusion that is shaped to interface with complementarily shaped protrusions of the input and output links while the transferred articulation force is below the predetermined level.

9. The surgical assembly of claim 3, wherein the spring assembly further includes a plurality of interface elements rotationally mounted to the base to rotate about the common axis of rotation, the combination of the interface elements and the spring inhibiting relative movement between the input link and the output link while the transferred articulation force is below the predetermined level and allowing relative movement between the input link and the output link when the transferred articulation force is above the predetermined level.

10. A surgical instrument for use with a robotic manipulator of a minimally invasive surgical system, the robotic manipulator having a holding fixture, the surgical instrument comprising:

an instrument shaft extending between a distal end and a proximal end;

an end effector supported by the distal end and including a jaw operable to grip a patient tissue;

a drive element drivingly coupled with the jaw;

a chassis disposed at the proximal end, the chassis including a frame supporting the instrument shaft, a spring assembly including an output link drivingly coupled with the drive element to induce a grip force of the jaw, an input link, and a spring having a first end and a second end, the first end being connected to the input link, the second end being connected to the output link, the spring assembly being configured to transfer an articulation force from the input link to the first end of the spring and transfer the articulation force from the second end of the spring to the output link, the output link being configured to transmit the articulation force to the jaw to induce the grip force of the jaw, the spring being preloaded so as to inhibit relative movement between the input link and the output link while the transferred articulation force is below a predetermined level and so as to allow relative movement between the input link and the output link when the transferred articulation force is above the predetermined level, and an input coupler drivingly coupled with the input link and configured to drivingly interface with a corresponding output coupler of the robotic manipulator; and wherein:

the drive element includes a drive shaft rotationally coupled with a grip mechanism configured to articulate the jaw; the input link and the output link are rotationally mounted to the frame to rotate about a common axis of rotation; and the spring includes a torsion spring.

11. The surgical instrument of claim 10, wherein:

a movement of the input link to further close the jaw when the transferred articulation force is at or above the predetermined level induces deformation of the spring associated with the relative movement between the input link and the output link so as to control an increase in transferred articulation force while the deformed spring transfers the articulation force from the input link to the output link.

12. The surgical instrument of claim 10, wherein the spring assembly further includes an interface element rotationally mounted to the frame to rotate about the common axis of rotation, the combination of the interface element and the spring inhibiting relative movement between the input and output links while the transferred articulation force is below the predetermined level and allowing relative movement between the input link and the output link when the transferred articulation force is above the predetermined level.

* * * * *